United States Patent
Gauthausen et al.

(10) Patent No.: US 7,397,241 B2
(45) Date of Patent: Jul. 8, 2008

(54) METHOD FOR DETERMINING THE CONTENT OF AT LEAST ONE COMPONENT OF A SAMPLE BY MEANS OF A NUCLEAR MAGNETIC RESONANCE PULSE SPECTROMETER

(75) Inventors: Gisela Gauthausen, Rheinstetten (DE); Andreas Kamlowski, Karlsruhe (DE); Dieter Schmalbein, Marxzell-Burbach (DE)

(73) Assignee: Bruker BioSpin GmbH, Rheinstetten-Forchheim (DE)

( * ) Notice: Subject to any disclaimer, the term of this patent is extended or adjusted under 35 U.S.C. 154(b) by 0 days.

(21) Appl. No.: 11/119,413

(22) Filed: Apr. 29, 2005

(65) Prior Publication Data

US 2005/0270026 A1 Dec. 8, 2005

(30) Foreign Application Priority Data

May 5, 2004 (DE) ............... 10 2004 022 687

(51) Int. Cl.
*G01V 3/00* (2006.01)
(52) U.S. Cl. ............... 324/307; 324/309; 324/300
(58) Field of Classification Search ......... 324/306–314, 324/303, 300, 318; 600/410, 413, 422
See application file for complete search history.

(56) References Cited

U.S. PATENT DOCUMENTS

| | | | | |
|---|---|---|---|---|
| 3,153,756 A * | 10/1964 | Williams et al. | ............. | 324/310 |
| 4,214,202 A * | 7/1980 | Bonori | ............. | 324/313 |
| 4,361,807 A * | 11/1982 | Burl et al. | ............. | 324/309 |
| 4,782,839 A * | 11/1988 | Hennig et al. | ............. | 600/413 |
| 5,023,551 A * | 6/1991 | Kleinberg et al. | ............. | 324/303 |
| 5,134,372 A | 7/1992 | Inoue | | |
| 5,201,311 A * | 4/1993 | Bottomley et al. | ............. | 600/422 |
| 5,270,650 A * | 12/1993 | Schenz et al. | ............. | 324/308 |
| 5,483,159 A * | 1/1996 | Van Heelsbergen | ............. | 324/318 |

(Continued)

FOREIGN PATENT DOCUMENTS

DE 39 19 052 C2 6/1989

(Continued)

OTHER PUBLICATIONS

Callaghan, Paul T., "Principles of Nuclear magnetic Resonance Microscopy", Oxford University Press, 1991.

(Continued)

*Primary Examiner*—Brij Shrivastav
*Assistant Examiner*—Tiffany A Fetzner
(74) *Attorney, Agent, or Firm*—Law offices of Paul E. Kudirka

(57) ABSTRACT

A method is described for determination of the content of at least one component of a sample by means of a nuclear magnetic resonance pulse spectrometer, with the magnetization of the sample being influenced by a sequence of radio-frequency pulses such that the signal amplitudes to be observed can be determined. The magnetization of the sample is initially saturated, and the signal amplitudes which are determined at each time by the longitudinal and transverse relaxation times $T_1$ and $T_2$ and/or $T_2^*$ and/or $T_{1\rho}$, from which a value for the content of the at least one component is determined, are measured at the same time in a cohesive experimental procedure.

11 Claims, 3 Drawing Sheets

U.S. PATENT DOCUMENTS

| | | | | |
|---|---|---|---|---|
| 5,565,775 | A | * | 10/1996 | Stallmach et al. ............ 324/303 |
| 5,602,477 | A | * | 2/1997 | McCarthy et al. ............ 324/315 |
| 6,232,778 | B1 | * | 5/2001 | Speier et al. ................ 324/303 |
| 6,320,377 | B1 | * | 11/2001 | Miyazaki et al. ............ 324/306 |
| 6,333,629 | B1 | * | 12/2001 | Pykett et al. ................ 324/307 |
| 6,859,033 | B2 | * | 2/2005 | Speier ........................ 324/303 |
| 6,911,822 | B2 | * | 6/2005 | Augustine et al. ........... 324/324 |
| 6,946,838 | B2 | * | 9/2005 | Corver et al. ............... 324/307 |
| 6,972,566 | B2 | * | 12/2005 | Guthausen et al. .......... 324/307 |
| 7,012,427 | B2 | * | 3/2006 | Augustine et al. ........... 324/307 |
| 7,199,581 | B2 | * | 4/2007 | Corver et al. ............... 324/308 |
| 2004/0041562 | A1 | * | 3/2004 | Speier ........................ 324/303 |
| 2004/0090231 | A1 | * | 5/2004 | Augustine et al. ........... 324/309 |
| 2004/0164736 | A1 | * | 8/2004 | Guthausen et al. .......... 324/307 |
| 2004/0251904 | A1 | * | 12/2004 | Corver et al. ............... 324/321 |
| 2005/0104589 | A1 | * | 5/2005 | Augustine et al. ........... 324/312 |
| 2005/0116712 | A1 | * | 6/2005 | Corver et al. ............... 324/309 |
| 2005/0270026 | A1 | * | 12/2005 | Guthausen et al. .......... 324/307 |
| 2005/0280414 | A1 | * | 12/2005 | Augustine et al. ........... 324/312 |

FOREIGN PATENT DOCUMENTS

| | | |
|---|---|---|
| DE | 41 33 643 C1 | 10/1991 |
| DE | 102 43 830 A1 | 9/2002 |
| DE | 103 04 184 A1 | 1/2003 |
| DE | 10 2004 022 687 A1 | 5/2004 |
| WO | WO 99/54751 A1 | 10/1999 |
| WO | WO 01/92908 A1 | 12/2001 |

OTHER PUBLICATIONS

Tinsley et al., "Evaluation of a Quantitative Magnetic Resonance Method for Mouse Whole Body Composition Analysis", Obesity Research, vol. 12, No. 1, NAASO, 2004.

Bruder et al., "A New Steady-State Imaging Sequence for Simultaneous Acquisition of Two MR Images with Clearly Different Contrasts", Magnetic Resonance In Medicine, vol. 7, Academic Press, Inc., pp. 35-42, 1988.

* cited by examiner

METHOD FOR DETERMINING THE CONTENT OF AT LEAST ONE COMPONENT OF A SAMPLE BY MEANS OF A NUCLEAR MAGNETIC RESONANCE PULSE SPECTROMETER

CROSS-REFERENCE TO RELATED APPLICATION

The present application claims priority of German patent application No. 10 2004 022 687.3 filed on May 5, 2004.

BACKGROUND OF THE INVENTION

The invention relates to a method for determination of the content of at least one component of a sample by means of a nuclear magnetic resonance pulse spectrometer, with the magnetization of the sample being influenced by a sequence of radio-frequency pulses such that the signal amplitudes to be observed can be determined.

A method of the type mentioned above, which is also referred to as time domain nuclear magnetic resonance measurement (time domain NMR, TD-NMR), is generally known and has been used for many years for the determination of the content of specific components in foods, for example for determination of the fat content in food products.

The time domain nuclear magnetic resonance measurement methods which have been used so far for determination of the fat or water content are restricted to samples which have a relatively low free water content of less than about 12%. This leads to the determination of the fat content of a food using a low-resolution nuclear magnetic resonance (NMR) pulse spectrometer in products with a high water content being made more difficult owing to the superimposition of the water and fat signals. Low-resolution nuclear magnetic resonance (NMR) pulse spectrometers are commercially available with a magnetic field strength of a maximum of about 1.5 Teslas and with a mean homogeneity of about $10^{-5}$ over the sample volume, and thus with a proton resonant frequency below about 60 MHz, for example the "minispec" from the Bruker Company. In other words, the determination of the fat content of samples with a relatively high water content is easily possible only by using high-resolution NMR spectrometers which, however, are generally much too expensive for this application, for example for foods chemistry.

In traditional time domain nuclear magnetic resonance (NMR) methods, only a single signal amplitude is obtained at a specific time or amplitude ratio and is compared with the results of a reference method for determination of the content of the component in the sample. For example, the oil content in seeds is determined by measurement of the spin echo amplitude for a specific echo time.

One possible way for also obtaining acceptable results for samples with a water content of more than about 12% by means of low-resolution nuclear magnetic resonance pulse spectrometers is to pre-dry the sample before the NMR measurement, for example in a drying oven, microwave drier or infrared drier, or by means of chemical drying, for example as described in DE 41 33 643 C1, in order to get rid of or at least to reduce the disturbing water component.

The disadvantage in this case is that the method for pre-drying requires a further process step which, depending on the method, is more or less labor-intensive and, furthermore, requires drying equipment where, in addition, the measurement process requires two much time owing to the pre-drying step, which is unacceptable for a large number of measurements which are required in the foods industry.

WO 99/54751 A1 and WO 01/92908 A1 describe NMR pulsed methods in which the different self-diffusion coefficient is also made use of, in addition to the different relaxation times $T_2$ of water and fat, in order to obtain a statement about the pure fat content. The entire content of these two documents is included in the disclosure content of the present application.

The basis of the methods which are known from the previously cited two documents for determination of the content of at least one component in a sample is the so-called PFGSE method (Pulsed Field Gradient Spin Echo), which is known per se from textbooks, for example from P. T. Callaghan: Principles of Nuclear Magnetic Resonance Microscopy, Oxford Science Publications, Clarendon Press, Oxford 1991 and in particular pages 162-169, 330-367, 371-417 and 478-482 there).

However, even the methods mentioned above which use the different self-diffusion coefficients in order to determine the content of at least one component in a sample have weaknesses.

Specifically, the gradient method that is described in these documents requires precise gradient control in order to produce the corresponding gradient pulses which, furthermore, themselves induce eddy currents in the apparatus, and these can adversely affect the measurement. Furthermore, the apparatuses that are currently commercially available are limited by the space required for the gradient coils, thus affecting the sample dimensions.

The known methods are based on the idea that only a single measurement is taken of a single relaxation time, that is to say the longitudinal relaxation time $T_1$ or the transverse relaxation time $T_2$.

Furthermore, the article by F. C. Tinsley et al., "Evaluation of a Quantitative Magnetic Resonance Method for Mouse Whole Body Composition Analysis" in Obesity Research, Vol. 12, No. 1, January 2004, describes a method in which the fat and water content of live mice is determined by means of an NMR pulse sequence, thus allowing the $T_1$ and $T_2$ influences to be measured. In this case, the measurement is calibrated using synthetic samples.

SUMMARY OF THE INVENTION

The invention is based on the object of specifying a method of the type mentioned initially which allows the content of at least one component of a sample to be measured reliably by means of a low-cost, low-resolution nuclear magnetic resonance pulse spectrometer, without any need to pre-dry the sample.

According to the invention, a method for determining the content of at least one component of a sample by means of a nuclear magnetic resonance pulse spectrometer is provided, comprising the steps of initially saturating the magnetization of the sample, influencing the magnetization by a sequence of radio-frequency pulses such that the signal amplitude to be observed can be determined, wherein the signal amplitudes which are determined at each time by the longitudinal and transverse relaxation time $T_1$ and $T_2$ and/or $T_2^*$ and/or $T_{1\rho}$, from which value for the content of the at least one component is determined, are measured at the same time in a cohesive experimental procedure.

A different approach is chosen for the method according to the invention, specifically the observation of the reduction in the magnetization from an initially saturated state (Mz=0). The content of the at least one component in the sample is, furthermore, determined by measuring different relaxation influences, specifically the relaxation of both the longitudinal and transverse magnetization. The NMR pulse sequence is preferably chosen such that the various NMR relaxation times $T_1$, $T_2$ and $T_2^*$ and/or $T_{1\rho}$ also influence the diffusion of the signal to be detected, as well as this being influenced by a possible static or time-dependent gradient. In this case, even if it is low, the spectral resolution of the NMR spectrum can also be used as a further contrast parameter for this purpose.

The method according to the invention makes it possible to simplify the measurement such that only a low-resolution NMR spectrometer is required, as is commercially available in a large number of optimal sample geometries. Furthermore, the measurement duration and the evaluation of the measurements require a short time in comparison to the drying method. In contrast to the article by F. C. Tinsley et al. as cited above, the present invention allows calibration using actual samples, which are characteristic of the reference methods to be used at the moment. The field of use of the method according to the invention is thus considerably widened, and it can be generalized to samples of different relaxation, such as those which can be observed, for example, in the polymer field, as well. Furthermore, other characteristics of the samples can be recorded by means of the pulse sequence that is used, for example the protein content of foods.

According to the invention, the magnetization of the sample is initially saturated in order subsequently to allow observation of the recovery of the magnetization, which distinguishes the method according to the invention from the known methods. Starting from saturated magnetization, which means that the magnetization is completely or substantially saturated, has the advantage that the repetition time between the individual measurements can be selected to be short, which thus means a time saving in comparison to a sequence starting from thermal equilibrium, which is significant in particular in the case of samples with a low signal intensity, that is to say a large number of individual experiments to be averaged. Depending on the sample to be examined, an additional variable $T_2^*(M(t,T_1^*)$ can be measured in addition to the parameters $T_1(M(t,T_2))$, $M(t,T_2^*))$, $T_2(M(t,T_1))$. The method according to the invention can be used, for example, to determine the water, fat and protein content in sausage samples, and the water and fat content in emulsions such as mayonnaises and sauces, as well as in margarines.

In one preferred refinement, the measured values which are obtained from the signal amplitudes and are determined by the relaxation times $T_1$ and $T_2$ and/or $T_2^*$ and/or $T_{1p}$ are analyzed by means of a chemometric method, using reference values from standard analysis methods on a sample of the same type as the sample to be measured.

In this case, it is advantageous that the measurement is evaluated using stored values from calibration samples of the same type as the measurement sample, thus making it possible to considerably widen the field of operation of the method according to the invention. Chemometric methods are preferably used for evaluation of the measurement, such as the PLS algorithm.

In further preferred refinements, the sample is additionally subjected to gradient fields in order to improve the contrast or in order to improve the saturation of the magnetization, in which case these gradient fields may be static or pulsed.

Further advantages and features will become evident from the following description of the attached drawings.

It is self-evident that the features mentioned already and those which are still to be explained in the following text can used not only in the respectively stated combination, but also in other combinations and on their own without departing from the scope of the present invention.

BRIEF DESCRIPTION OF THE DRAWINGS

Exemplary embodiments of the invention will be explained in more detail in the following description, and are illustrated in the drawing, in which.

DETAILED DESCRIPTION OF PREFERRED EMBODIMENTS

Figure 1:
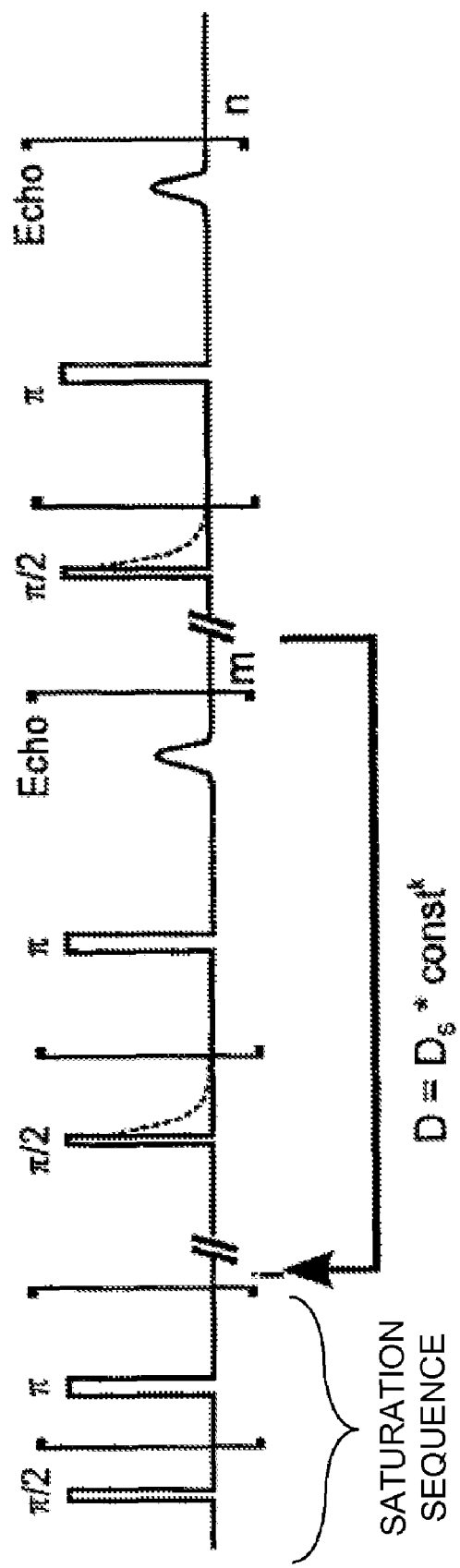
FIG. 1 shows a pulse sequence for measurement of the water, fat and/or protein content of sausage samples.

FIG. 1 shows, schematically, a pulse sequence which is used for the method according to the invention.

One major feature of the method according to the invention is that the combination of various relaxation processes, that is to say the signal amplitudes (these are, for example, governed by the $T_1$ and $T_2$ relaxation), that is to say the mutual relationship between the parameters, is taken into account.

This is because it has been found that poorer measurement results are obtained when only one measurement of the longitudinal or of the transverse magnetization decay is carried out. Furthermore, it has been found that the best correlation between the measurement sample and the reference sample is obtained when the combined magnitization decays are investigated, that is to say the correlation is improved when the combined information from $T_1$ and $T_2$ relaxation is used. Since the relaxation times reflect both dynamic aspects of the examined molecules and static characteristics of their environments, it can be expected that minor changes in the sample composition significantly affect the relaxation, even though the content of the component to be determined remains constant. The combined method, as used in the present invention for examination of the relaxation of both $T_1$ and $T_2$ relaxation processes is thus considerably more sensitive than the component to be measured quantitatively.

The pulse sequence illustrated in FIG. 1 starts with a saturation pulse sequence, by means of which the magnetization of the sample is saturated. This sequence comprises a high-frequency π/2 pulse followed by a series of i π pulses. This saturation sequence is then repeated in a known fashion. However, in each repetition, there may be different numbers of, π pulses, such as m or n pulses, in the series. The saturation pulse sequence which is used here leads on the one hand to the repetition time been shortened while, on the other hand, it results in a reproducible magnetization state.

The number of saturation pulses and time interval chosen between them, which is often aperiodic, are optimized depending on the sample to be examined. Starting from this saturated state of magnetization, which in fact need not be complete, the detection sequence is carried out, essentially comprising $T_1$-weighted measurements of the transverse relaxation in multiple echo conditions. In particular. detection is started after a relaxation delay time D which is equal to the relaxation delay after the saturation sequence ($D_s$) multiplied by a constant (const) raised to a rower k that is dependent on the chosen number of relaxation delays (k) before the detection sequence is begun. ($D=D_s * \text{const}^k$).

The free induction decay (FID) shown by dashed lines in FIG. 1 can be acquired in order to record quickly relaxing components of the sample to be measured. This is advantageous, for example, for protein determination. The time parameters and the number of echoes to be measured are once again matched to the sample to be examined.

At the end of the pulse sequence, when the magnetization is in thermal equilibrium, a complete transverse magnetization decay is digitized, and the time intervals and the number of echoes are adapted on a sample-specific basis.

It should be mentioned that the echo times for the echoes which are digitized in dynamic equilibrium and in thermal equilibrium need not be identical, so that relaxation effects can also be recorded using the rotating coordinate system.

In addition, instead of evaluation using the time signals, a Fourier transformation can be carried out in the frequency domain, so that the spectroscopic information (even if there is little of it) of the low-field spectra can also be used as an additional contrast parameter.

Furthermore, the pulse sequence can be extended by the corresponding pulsed gradients in the loops of the transverse relaxation (with the indices m, n), so that diffusion information is accessible. If the information from the FIDs is dispensed with, it is also possible to operate with static gradients. Furthermore, the saturation of the magnetization can also be completed by the use of gradients.

Figure 2:
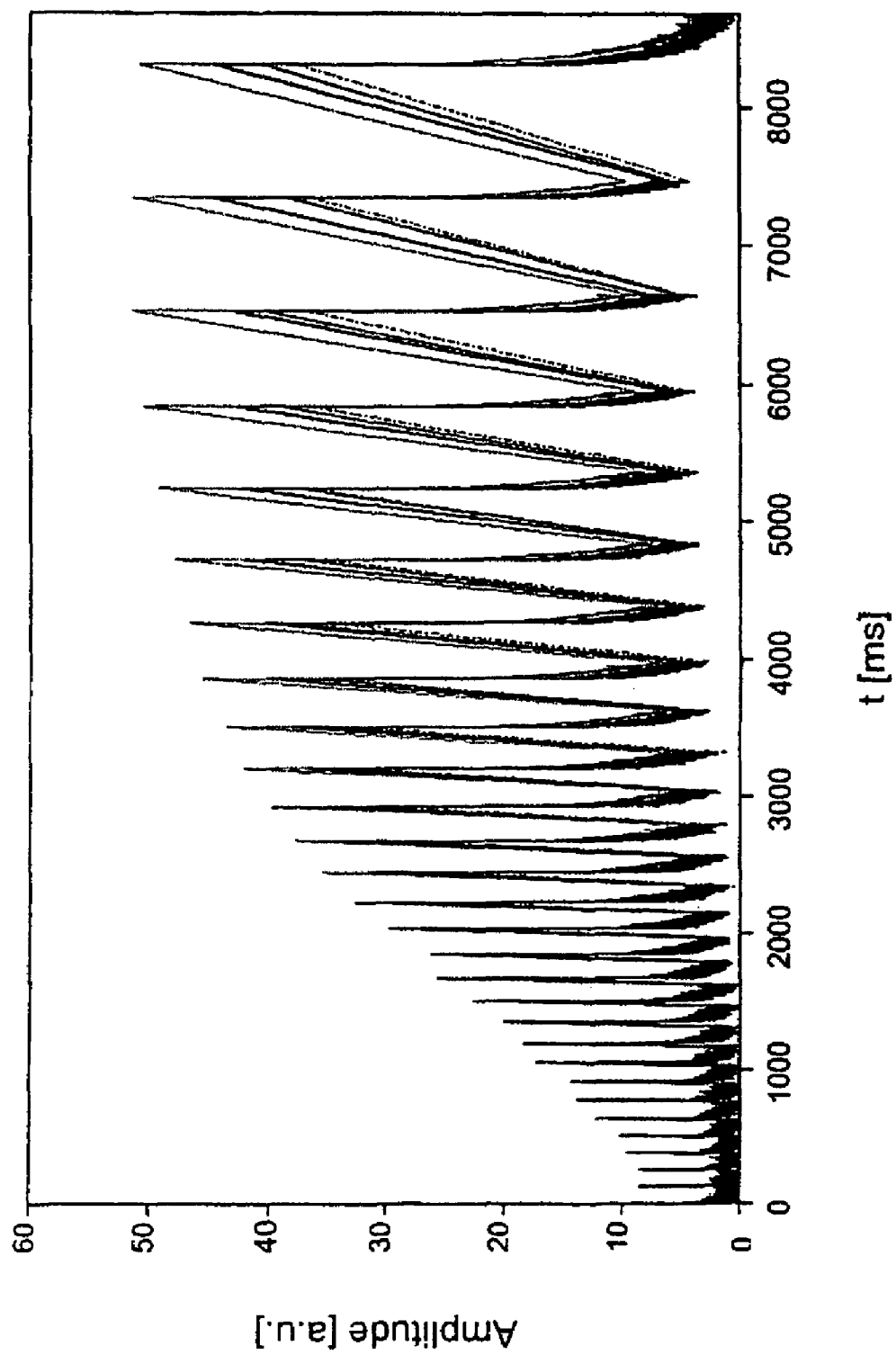
FIG. 2 shows an illustration of the raw NMR data, as is available for evaluation on the basis of the respective relaxation characteristics of a sample.

FIG. 2 shows the raw data for samples with different water, fat and protein contents. The graph shows the signal amplitude as a function of the measurement time. This clearly shows the relaxation differences and different signal amplitudes for the different samples.

The evaluation of the relaxation spectra is carried out in the present case using chemometric methods, but it is also possible to use methods such as inverse Laplace transformation or other analytical methods.

The chemometric approach has the advantage that the method results in a data reduction which, with the other methods, would have to be implemented by means of algorithms to be developed in-house and which, in some circumstances, will be dependent on the respective relaxation parameters of the samples to be examined.

Figures 3A, 3B, 3C:
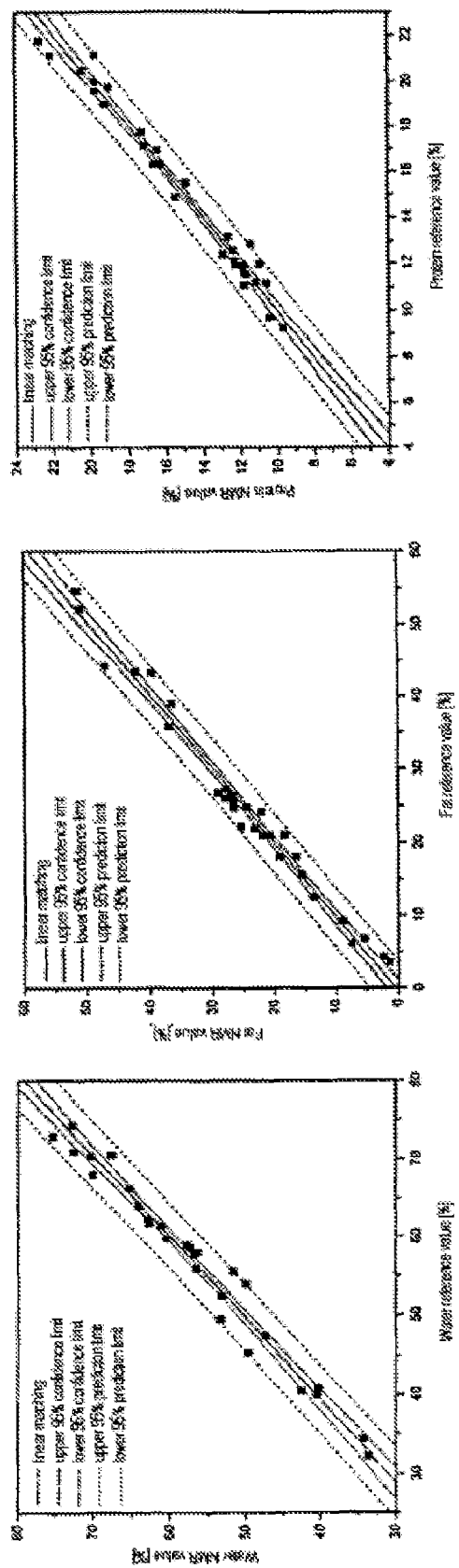
FIG. 3A shows a correlation of NMR signals representing the percentage of water in thirty sausage samples with percentage values obtained from conventional chemical analysis.
FIG. 3B shows a correlation of NMR signals representing the percentage of fat in thirty sausage samples with percentage values obtained from conventional chemical analysis.
FIG. 3C shows a correlation of NMR signals representing the percentage of protein in thirty sausage samples with percentage values obtained from conventional chemical analysis.

FIGS. 3A, 3B and 3C are correlation diagrams with the corresponding prediction values, for percentages of water, fat and protein, respectively, as were obtained from the analysis of 30 different sausage samples both by the inventive NMR technique (NMR values) and by conventional chemical analysis (reference values). Each figure shows thirty values plotted with the NMR values on the vertical axis and the reference values plotted on the horizontal axis. A curve has been drawn through the resulting points using linear matching and upper and lower bounds for 95% confidence and 95% prediction factors have been computed using conventional statistical software and are also shown in each figure. The conventional correlation and F-factors are also noted.

In this case, the signal contributions had different weightings for different measurement temperatures, so that the correlation results were found to be dependent on the measurement temperature. This characteristic of temperature dependency can be used in order to optimize the contrast for the type of sample to be measured in any specific case.

It should be mentioned that the choice of the sequence parameters also has a significant influence on the contrast.

The evaluation process was carried out using the "Bruker Opus-Quant 2" software, which is software for chemometric data processing, and was optimized with the aid of the pre-processing options implemented there, such as the formation of the derivative or baseline correction.

The chemometric evaluation process results in the content of the components in the sample from the NMR measurement, which is compared with the reference value, to be precise for all the measured samples, and a statement about the quality of the method for the determination of the individual components is obtained over the illustrated correlation graphs. In this case, the correlation coefficient and the F factor, which reflects the statistical relevance of the measurement, are obtained by linear regression.

In addition, the figures also show the values for a 95 percent probability, and the 95 percent confidence interval, as a function of the reference value.

What is claimed is:

1. A method for quantitatively determining an amount of at least one constituent of a sample by means of a nuclear magnetic resonance pulse spectrometer, comprising the steps of:
   (a) placing the sample in a static magnetic field in order to cause a net magnetization in the sample to be aligned with the static magnetic field;
   then in a single cohesive NMR experimental procedure:
   (b) substantially saturating the magnetization of the sample by an initial saturation sequence of radio frequency pulses;
   (c) after step (b), applying a contiguous sequence of radio-frequency pulses;
   (d) measuring signal amplitudes produced by the contiguous sequence of radio-frequency pulses, during the single cohesive NMR experimental procedure, wherein the signal amplitudes of each amplitude measurement are dependent on both a longitudinal relaxation time T1 and at least one additional relaxation time selected from the group consisting of T2, T2* and Tlp; and subsequently
   (e) determining the amount of the at least one constituent in the sample from the measured signal amplitudes provided by the contiguous sequence of RF pulses from the single cohesive NMR experimental procedure using statistical methods.

2. The method of claim 1, wherein step (e) comprises analyzing the measured signal amplitudes by means of a chemometric method, using reference values from standard analysis methods performed on a reference sample of the same type as the sample.

3. The method of claim 1, wherein the sample is additionally subjected to gradient fields in order to improve the contrast.

4. The method of claim 3, wherein the gradient fields are static.

5. The method of claim 3, wherein the gradient fields are pulsed.

6. The method of claim 1, wherein the sample is additionally subjected to gradient fields in order to improve the saturation of the magnetization.

7. The method of claim 6, wherein the gradient fields are static.

8. The method of claim 6, wherein the gradient fields are pulsed.

9. The method of claim 1, wherein the nuclear magnetic resonance pulse spectrometer used has a low resolution.

10. The method of claim 1, wherein the sample is a foodstuff, and the at least one constituent is at least one of fat, water and a protein.

11. The method of claim 1, wherein the sample is a polymer.

* * * * *

UNITED STATES PATENT AND TRADEMARK OFFICE
CERTIFICATE OF CORRECTION

| | |
|---|---|
| PATENT NO. | : 7,397,241 B2 |
| APPLICATION NO. | : 11/119413 |
| DATED | : July 8, 2008 |
| INVENTOR(S) | : Gisela Guthausen, Dieter Schmalbein and Andreas Kamlowski |

It is certified that error appears in the above-identified patent and that said Letters Patent is hereby corrected as shown below:

Title Page, Item 75,

Please replace "Gauthausen" with --Guthausen--.

Signed and Sealed this

Thirtieth Day of December, 2008

JON W. DUDAS
*Director of the United States Patent and Trademark Office*